United States Patent [19]

Sih

[11] Patent Number: 5,219,731

[45] Date of Patent: Jun. 15, 1993

[54] METHOD FOR PREPARING OPTICALLY-ACTIVE AMINO ACID DERIVATIVES

[75] Inventor: Charles J. Sih, Madison, Wis.

[73] Assignee: Wisconsin Alumni Research Foundation, Madison, Wis.

[21] Appl. No.: 786,731

[22] Filed: Nov. 1, 1991

[51] Int. Cl.$^5$ .......................... C12Q 1/34; C12Q 1/37
[52] U.S. Cl. .......................................... 435/18; 435/24
[58] Field of Search ...................................... 435/18, 24

[56] References Cited

FOREIGN PATENT DOCUMENTS

```
62-129238   6/1987   Japan .
2215391     8/1990   Japan .
2234685     9/1990   Japan .
9015146    12/1990   PCT Int'l Appl. .
```

OTHER PUBLICATIONS

McGahren et al. Tetrahedron 23, 2017 (1967).
Chibata et al., J. Appl. Microbiol., 13, 638 (1965).
T. Fukumura Agric. Biol. Chem. 41, 1321 & 1327 (1977).
de Jersey et al. Biochemistry 8, 1967 (1969).
Sih et al. J Indus Micro, Suppl 3, Develop Ind Micro 29, 221–229, (1988).
Bevinakatti, H. S. et al., "Lipase–catalyzed Enantioselective . . . " *J. Chem. Soc., Chem. Comm.*, 1990, pp. 1091–1029.
O'Donnell, M. J. et al., "Stereoselective Synthesis . . . ", JACS v. 111:6, pp. 2353–2355, 1989.
Daffe, V. et al. "Enantiomeric Enrichment . . . ", JACS v. 102:10, pp. 3601–3604, 1980.

*Primary Examiner*—Michael G. Wityshyn
*Assistant Examiner*—Ralph Gitomer
*Attorney, Agent, or Firm*—Olson & Hierl, Ltd.

[57] ABSTRACT

The invention relates to a method for enzymatically producing directly optically-active amino acid derivatives in high optical purity from oxazolone precursors. Thus, such a precursor is subjected to the presence of a catalytically effective amount of a selected enzyme in a mutual solvent. The cyclic precursor is enantioselectively cleaved by hydrolysis. Subsequently, the desired optically-active amino acid derivative is recovered. A preferred cyclic precursor is a 5(4H)-oxazolone compound and a preferred enzyme is a lipase. Either aqueous or organic solvent media can be used.

37 Claims, No Drawings

METHOD FOR PREPARING OPTICALLY-ACTIVE AMINO ACID DERIVATIVES

This invention was made with United States Government support awarded by the National Institute of Health (NIH), Grant No. RO1-GM33149-11. The United States Government has certain rights in this invention

FIELD OF THE INVENTION

This invention relates to the preparation of optically active amino acids in substantial enantiomeric excess from an enantioselective ring opening of cyclic precursors. More specifically, 5(4H)-oxazolones are asymmetrically hydrolyzed in the presence of a lipase.

BACKGROUND OF THE INVENTION

Optically-active amino acids in high purity are becoming increasingly important as intermediates for the preparation of pharmaceuticals, foods and agrochemicals. Hoppe et al., *Chemie in Unserer Zeit*, 17, 41–53 (1983); and Kleeman et al., in *Ullmann's Encyclopedia of Industrial Chemistry*, Vol. A2, pages 57–97.

For example, D-phenylglycine and D-p-hydroxyphenylglycine are side chain precursors for the semisynthetic penicillins, ampicillin and amoxycillin, respectively. See Schmidt-Kastner et al., in *Biotechnology*, Vol. 6a, edited by H. J. Rehm and G. Reed, Verlag Chemie, pages 388–419 (1984). In addition, the most important building block for the low-calorie sweetener, aspartame, is L-phenylalanine. Mazur et al., *J. Am. Chem. Soc.*, 91, 2684 (1969). Moreover, D-phenylalanine possesses analgesic properties and might one day supplant aspirin [*Nutrition News*, Vol. VI, no. 7 (1983)]; and D-valine is an intermediate for the pyrethroid insecticide, Fluvalinate [*Farm. Chem. Handbook*, 72nd ed., Meister Publ. Co. (1986)].

Examples of essential amino acids which are important in human nutrition include L-isoleucine, L-leucine, L-lysine, L-methionine, L-phenylalanine, L-threonine, L-tryptophan and L-valine. The uses of these essential amino acids have been described in several review articles. Izumi et al., *Angew. Chem. Int. Ed. Eng.*, 17, 176 (1978); and Drauz et al., ibid., 21, 584 (1982).

For many applications, it is necessary to have an optically active amino acid as the starting material which has an optical purity of at least about 65 percent and preferably at least about 90 percent. Such a purity level appears to be a requirement particularly in the case of optically active acyl amino acids.

There are essentially four processes that are used for the production of amino acids. These comprise: a) extraction; b) chemical synthesis; c) fermentation; and d) enzymatic catalysis.

In the extraction process, the natural L-amino acids are isolated from protein-containing animal and vegetable products. However, because of the high production costs, only the amino acids, L-cystine, L-tyrosine and L-proline can be economically produced using this method. Kleeman et al., *Ullmann's Encyclopedia of Industrial Chemistry*, Vol. A2, page 67.

In principle, all amino acids can be prepared by chemical asymmetric syntheses. However, the only process that has provided for large-scale production is the production of L-dopa via hydrogenation in the presence of an optically-active rhodium complex. Knowles et al., *J. Am. Chem. Soc.*, 99, 5946 (1977). The more common chemical methods are optical resolution by direct crystallization of enantiomeric mixtures, Collet et al., *Chem. Rev.*, 80, 215 (1980), and fractional crystallization of diastereomeric salt pairs as disclosed in U.S. Pat. No. 4,224,239 to Nippon Kayaku. However, all of these processes are expensive and are not universally applicable.

The fermentation process is used commercially only for the biosynthesis of natural L-amino acids. The fermentation equipment used in the process is expensive. And the lower yields of other amino acids using this process make it economically prohibitive.

The fourth process of amino acid production involves enzymatic catalysis. The general principles of the catalysis are well known in the art and include use of the following enzymes to provide the L-amino acid as one of the reaction products: (1) an L-specific esterase; (2) an L-specific acylase; (3) a nitrile hydratase followed by an amidase; and (4) an aminopeptidase.

However, there are several disadvantages associated with use of an enzymatic catalysis process. Since it is a kinetic resolution procedure, the desired enantiomer can be obtained in only 50 percent theoretical yield. Moreover, tedious separation of the acid from the ester or amide is required. The undesired enantiomer is isolated and racemized again for recycling.

Most enzymatic catalysis processes are designed for the synthesis of a particular amino acid. For example, L-aspartic acid is prepared industrially via stereospecific amination using aspartase from *E. coli*: L-aspartate in turn can be transformed into L-alanine with an L-aspartate-$\beta$-decarboxylase from *Pseudomonas dacunhae*, Chibata et al., *J. Appl. Microbiol.*. 13. 638 (1965).

For another example, a combination of chemical and microbiological methods is used for the synthesis of L-lysine. Thus, DL-$\alpha$-amino-$\epsilon$-caprolactam is obtained from cyclohexane in three steps. Hydrolysis of the L-isomer by cells of *Candida humicola* containing L-specific $\alpha$-amino-$\epsilon$-caprolactamase produces L-lysine. The D-$\alpha$-amino-$\epsilon$-caprolactam is racemized by a racemase from *Alkaligenes faecalis*, T. Fukesmura, *Agric. Biol.* Chem., 41, 1321 and 1327 (1977). This process is used by Toray industries for commercial scale L-lysine production.

For an additional example, a biochemical method for the production of L-serine from DL-oxazolidine-4-carboxylic acid is known. This procedure involves the hydrolysis of the L-oxazolidine into L-serine by *Pseudomonas testosteroni*. The D-oxazolidine is racemized to DL-oxazolidine by a racemase from *Bacillus subtilis*, Yokozeki et al., *Agric. Biol. Chem.*, 51, 963 (1987).

A Similar enzymatic process was developed for the commercial production of L-cysteine from DL-2-aminothiazoline-4-carboxylic acid (DL-ATC). In this case, both the L-ATC hydrolase and ATC racemase reside in the same microorganism, *Pseudomonas thiazolinophilum*, Sano et al., *Agric. Biol. Chem.*, 43, 2373 (1979).

A more general biocatalytic asymmetric process is based on the stereospecific action of microbial hydantoinases. In this process, the nonreactive hydantoin antipode is racemized under the reaction conditions or via the action of a racemase. Apparently, this methodology is commercialized only for the production of D-phenylglycine and D-p-hydroxyphenylglycine. The disadvantage of this process is that the hydantoinases are substrate-specific which requires tedious screening to find hydantoinases for the synthesis of each amino acid in the enantiopure form.

A specific enzymatic catalysis process which has received considerable attention over the past several years is the use of a lipase to stereoselectively hydrolyze esters. Lipases are well known and many of these are available commercially. The properties of lipases, in particular their biochemical actions, are described by H. L. Brockman in *Lipases* edited by B. Borgstrom and H. L. Brockman, Elsevier, Amsterdam, p. 3 (1984). Lipases are used commercially for the transesterification of fats and are incorporated in laundry detergents for removal of oily contaminants.

One example of a catalyzed process using a lipase is disclosed in WO 9015146. Racemic mixtures of esters of 2-substituted acids, other than 2-halopropionic acids, are stereoselectively hydrolyzed in the presence of a lipase of *Candida rugosa* in an organic solvent. Preferably, the process is carried out in a reducing agent to yield high optical purity.

Another specific enzymatic catalysis process using a lipase is disclosed in Japanese Patent No. 2215391. The lipase of *Candida cylindracea* was used to hydrolyze N-acyl-amino acid esters to produce glycine. The reaction was carried out at room temperature and the yields were about 70 percent.

The 5(4H)-oxazolones, commonly known as azlactones, and as exemplified by Formula (1) herein, are useful intermediates in the synthesis of α-amino acids and peptides. They can undergo ring opening with various nucleophiles such as water, alcohols, amines, thiols, amino acid esters, and the like to produce amino acid derivatives.

In principle, if the unreactive azlactone is racemized in situ under the reaction conditions, quantitative transformations of a racemic azlactone by a suitable biocatalyst (enzyme) is possible. The behavior of azlactones towards proteolytic enzymes and carboxyesterase has been examined. However, the reactions were carried out in dilute mixtures because the reaction rate is slow. Moreover, the optical purity of the product is not sufficiently high for industrial use, de Jersey et al., *Biochemistry*, 8, 1967 (1980); *ibid.*, 9, 1761 (1970); Daffe et al., *J. Am. Chem. Soc.*, 102, 3601 (1980).

In fact, in a very recent publication, Bevinakatti et al., *J. Chem. Soc. Chem. Commun.*, 1091 (1990), it is stated that, "Because azlactones undergo spontaneous hydrolysis in the presence of water, previous attempts (referring to de Jersey et al. and Daffe et al.) to cleave them enantioselectively using enzymes or cyclodextrins as catalysts have met with little success." In an attempt to overcome this problem of spontaneous hydrolysis of azlactones in aqueous media, Bevinakatti et al. carried out their reactions in anhydrous organic solvents. They attempted the enzyme-catalyzed enantioselective ring-opening of 2-phenyl-4-methyl-oxazolin-5-one using butan-1-ol as the nucleophile in diisopropyl ether (DIPE) as solvent.

Bevinakatti et al. found that the lipases of *Candida cylindracea* (CCL) and porcine pancreatic lipase (PPL) quantitatively transformed the azlactone, 2-phenyl-4-methyl-oxazolin-5-one, into R-butyl-N-benzoylalanine: but the enantiomeric excess (ee) was found to be only 10 percent and 3 percent, respectively. On the other hand the lipase of *Mucor miehei* converted the same azlactone into S-butyl-N-benzoylalanine with an optical purity of 57 percent ee at 45 percent conversion but reduced to 34 percent ee at 100 percent conversion. These results clearly demonstrate that the Bevinakatti et al. process is unsuitable for producing optically-active acyl amino acids having the foregoing required high optically-active purity levels.

The art needs a new and useful process for producing optically-active acyl amino acids from oxazolone precursors.

SUMMARY OF THE INVENTION

The present invention relates to an enzymatic method for directly producing optically-active amino acids, such as optically-active acyl amino acids, in high optical purity by contacting an oxazolone precursor of the particular amino acid desired with a selected enzyme in a mutual solvent to enantioselectively cleave the oxazolone precursor. The optically active amino acid derivative produced is recovered from the mixture produced.

The selected enzyme is hydrolytically active and induces an oxazolone ring to cleave and rearrange to a desired optically-active amino acid, such as an optically active acyl amino acid.

The practice of the inventive method provides for the direct production of optically-active amino acids having optical purities of at least about 65 percent, and preferably at least about 90 percent. So far as now known, no one has heretofore ever produced directly by enzyme catalysis optically-active amino acids of such optical purity levels. Thus, the product optically-active amino acids are directly usable for many industrial and commercial applications without further intervening purification.

More particularly, the present invention relates to a method for preparing optically-active amino acid derivatives in a substantial enantiomeric excess (as further defined herein). A cyclic precursor of an amino acid is subjected to the presence of a catalytically effective amount of an enzyme in a mutual solvent. The cyclic precursor is enantioselectively cleaved by hydrolysis. Subsequently, the desired optically-active amino acid derivative is recovered.

Enzymes with such characteristics include lipases and proteases. Certain lipases are presently preferred. The enzyme is contacted with the cyclic oxazolone precursor in an aqueous or organic solvent.

One feature of lipases is that they can tolerate high substrate and product concentrations. Thus, no marked substrate and no product inhibition are generally observed, and the enzymatic hydrolytic reaction can be conducted with high substrate concentrations of about 0.1 to 1 M with a high degree of stereoselectivity. Moreover, lipases are remarkably stable under the reaction conditions described herein, so they can be reused.

A preferred cyclic amino acid precursor is a 5(4H)-oxazolone having the following formula:

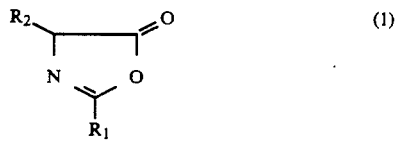

(1)

where $R_1$ and $R_2$ are each a monovalent organo moiety that is substantially inert in the presence of a hydrolytically active enzyme as described herein.

In a more preferred embodiment, $R_1$ can comprise hydrogen; a phenyl group; an alkyl or alkenyl radical of less than about ten carbon atoms; or an araliphatic radical having a phenyl group and an alkylene group of less than about three carbon atoms. Moreover, $R_1$ can comprise an alkyl or alkenyl radical of less than about ten carbon atoms substituted with one or two carboxylic acid groups; or an araliphatic radical having a phenyl group and an alkylene group of less than about three carbon atoms substituted by one or two carboxylic acid groups.

$R_1$ can also comprise an alkyl or alkenyl radical of less than about ten carbon atoms substituted by one or two ester groups; an araliphatic radical having a phenyl group and an alkylene group of less than about three carbon atoms substituted by one or two ester groups, an alkyl or alkenyl radical of less than about ten carbon atoms substituted with one or more carboxylic acid esters; and an araliphatic radical having a phenyl group and an alkylene group of less than about three carbon atoms substituted with one or two carboxylic acid esters.

In the more preferred embodiment, $R_2$ can comprise a phenyl group; an alkyl or alkenyl radical of less than about ten carbon atoms; an araliphatic radical having a phenyl group and an alkylene group of less than about six carbon atoms. $R_2$ can also comprise a heterocyclic radical derived from a heterocyclic compound that is selected from the group consisting of indole, pyrrole, isoindole, indolizine, furan, benzofuran, pyridazine, triazole, thiazole, oxazole, pyrazole, isoxazole, isothiazole, thiophene, pyridine and indoline.

One significant advantage of this invention over the methods of the prior art is the production of optically-active amino acid derivatives in a substantial enantiometric excess using an enzymatic asymmetric hydrolysis process.

Another advantage of this invention is that it makes available a commercially feasible catalytic process for preparing optically-active amino acids using relatively inexpensive lipases.

These and other objects, purposes, features, benefits, advantages and the like of this invention will become apparent to those skilled in the art from the following description.

DETAILED DESCRIPTION

The present invention relates to the enantioselective ring opening or cleaving of a cyclic amino acid precursor by hydrolysis catalyzed by an enzyme. The cyclic precursor is preferably a heterocyclic compound comprising an oxazolone.

The present optically-active amino acid derivative is prepared in a substantial enantiomeric excess. As used herein, the term "substantial enantiomeric excess" refers to an optical purity of at least about 65 percent. More preferably, the optically-active amino acid derivatives according to this invention are prepared in an enantiomeric excess of at least about 90 percent.

The oxazolone compounds preferably correspond to the general Formula (1) shown above and react to produce an optically-active acyl amino acid product illustrated by the following exemplary equation:

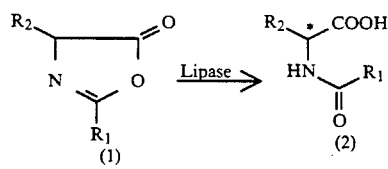

In the product of Formula (2), $R_1$ and $R_2$ are each as above defined.

In a more preferred embodiment, $R_1$ is selected from the group consisting of hydrogen; a phenyl group; an alkyl radical of less than about ten carbon atoms; an alkenyl radical of less than about ten carbon atoms; an alkyl radical of less than about ten carbon atoms substituted by at least one halogen; an alkenyl radical of less than about ten carbon atoms substituted by at least one halogen; an araliphatic radical having a phenyl group and an alkylene group of less than about three carbon atoms; an alkyl radical of less than about ten carbon atoms substituted with one or two carboxylic acid groups; an alkenyl radical of less than about ten carbon atoms substituted with one or two carboxylic acid groups; an araliphatic radical having a phenyl group and an alkylene group of less than about three carbon atoms substituted by one or two carboxylic acid groups; an alkyl radical of less than about ten carbon atoms substituted by one or two carboxylic acid ester groups; an alkenyl radical of less than about ten carbon atoms substituted with one or two carboxylic acid ester groups; an araliphatic radical having a phenyl group and an alkylene group of less than about three carbon atoms substituted by one or two carboxylic acid ester groups; an alkyl radical of less than about ten carbon atoms substituted with one or more carboxylic acid ester groups; an alkenyl radical of less than about ten carbon atoms substituted by one or two carboxylic acid ester groups; and an araliphatic radical having a phenyl group and an alkylene group of less than about three carbon atoms substituted with one or two carboxylic acid ester groups.

The term "phenyl group" as used herein has reference to both unsubstituted and substituted phenyl nuclei. Although unsubstituted phenyl groups are now preferred generally, one presently preferred class of substituted phenyl nuclei comprises mono- or di- substituted phenyl nuclei wherein each substitutent is a lower alkyl group (that is, an alkyl group containing less than about five carbon atoms).

The term "carboxylic acid group" as used herein has reference to both a carboxylic acid moiety (that is, —COOH) and water soluble salts thereof (that is, groups of the formula —COOM where M is an alkali metal or ammonium).

The term "carboxylic acid ester" as used herein preferably has reference to a moiety having the structure —$COOR_3$ where $R_3$ is an alkyl group containing less than about five carbon atoms. When more than two carboxylic acid ester groups are present in an alkyl or alkenyl radical (as above defined), preferably not more than three carboxylic acid ester groups are present.

In addition, in such a more preferred embodiment, $R_2$ is selected from the group consisting of a phenyl group; an alkyl radical of less than about ten carbon atoms; an alkenyl radical of less than about ten carbon atoms; an alkyl radical of less than about ten carbon atoms substituted with sulfur, a nitrogen containing group, oxygen, or a halogen; an alkenyl radical of less than about ten carbon atoms substituted with sulfur, a nitrogen containing group, oxygen, or a halogen; an araliphatic radical having a phenyl group and an alkylene group of less than about six carbon atoms; an araliphatic radical having a phenyl group and an alkylene group of less than about six carbon atoms wherein the phenyl group is substituted with a sulfur containing group, a nitrogen containing group, an oxygen containing group, a hydroxyl group, a methoxyl group or a halogen. $R_2$ can also comprise a heterocyclic radical derived from a heterocyclic compound that is selected from the group consisting of indole, pyrrole, isoindole, indolizine, furan, benzofuran, pyridazine, triazole, thiazole, oxazole, pyrazole, isoxazole, isothiazole, thiophene, pyridine and indoline; a selected heterocyclic radical substituted with an alkyl group of less than about five carbon atoms; a selected heterocyclic radical substituted with an alkenyl group of less than about six carbon atoms; and a selected heterocyclic radical substituted with a halogen.

When $R_1$ comprises an alkyl or alkenyl radical of less than about ten carbon atoms, it is preferred that these radicals be substituted with a halogen. The preferred halogen substituent in all instances is either fluorine or chlorine.

When $R_2$ is a heterocyclic radical as above identified, it is preferred that the radical be substituted. An alkyl or alkenyl radical of less than about five carbons and a halogen are preferred substituents.

The more preferred substituents for the above Formula (1) and (2) are those where $R_1$ is phenyl and $R_2$ is phenyl, benzyl, indolyl, methoxyphenyl, thioalkyl, methoxyindolyl, an n-alkyl or a branched allyl.

A racemic mixture of the cyclic amino acid precursor of Formula (1) can be used in the present invention. Preferably, the racemic mixture undergoes in situ conversion to complete the hydrolysis.

An alkyl group is a paraffinic hydrocarbon group which may be derived from an alkane by dropping one hydrogen from the formula. A alkenyl group is a monounsaturated alkyl group. An araliphatic group can also be referred to as an arylalkylene or an aralkyl group and designates a radical containing both an aliphatic and aromatic structure. A heterocyclic radical designates a closed ring structure, usually of either five or six members, in which one or more of the atoms in the ring is an element other than carbon. The branched allyl group includes an allyl group that is substituted with an aralkyl group such as a group that is derived from a compound of the formula:

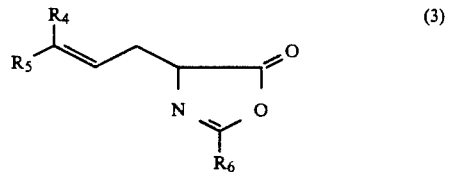

(3)

wherein:

$R_4$ and $R_5$ are each either hydrogen or an alkyl group containing less than six carbon atoms; and $R_6$ is an araliphatic group having a phenyl group and an alkylene group of less than about six carbon atoms.

Several conventional methods can be employed for the preparation of the $(\pm)5(4H)$-oxazolone substrates of Formula (1); see, for example, J. P. Greenstein, *Chemistry of the Amino Acids.* Vol. 2, pp. 823-843, John Wiley & Sons, NY (1961); Roa et al., in *Oxazoles,* I. J. Turchi, ed., Vol. 45, pp 361-730, Wiley, NY (1986); and McGahren et al., *Tetrahedron,* 23, 2017 (1967).

An exemplary procedure according to the method of this invention is provided below.

About 50 mg of an oxazolone precursor (the Formula (1)) and about 50 mg of the enzyme are incubated in 2 ml 0.2 M (pH 7.6) aqueous phosphate buffer at about 25° C. or the like to preferably 100 percent conversion. The weight ratio of the Formula (1) compound to the enzyme can vary. The reaction is conveniently monitored by thin layer chromatography using, for example, 40 percent ethyl acetate in hexane. The reaction mixture is acidified with 2N HCl or the like, and then is extracted with ethyl acetate or the like, dried over magnesium sulfate or the like, and preferably evaporated to dryness in vacuo. After purification by chromatography (for example, as outlined in Example 1 below) or the like, rotation is conveniently checked in methanol, and the ee can be determined by NMR.

The 5(4H)-oxazolone Formula (1) substrate can be added in solid or liquid form in an aqueous solvent. With a suitable buffer solution containing the enzyme (preferably, a lipase), a substrate concentration in the range of about 0.1 M to about 1 M is preferred. Alternatively, the substrate can be dissolved in a suitable organic solvent, such as carbon tetrachloride, cyclohexane, carbon disulfide, hexane or the like, as long as the solvent does not denature the enzyme. In addition, the substrate can be emulsified by the use of an emulsifier, such polyvinyl alcohol, propylene glycol, or the like.

Of course, the temperature and pressure conditions under which the contact of the substrate with the lipase occurs are interdependent as will be apparent to those skilled in the art. Generally, at atmospheric pressure, the temperature is in the range of about 10° C. to about 40° C. and the pH of the solvent is in the range of about 3 to about 10. A more desirable pH range is from about pH 7 to about 8 with a presently most preferred pH being about 7.8.

Where an optically-active amino acid product produced by the practice of the method of this invention has an enantiomeric excess (ee) of less than about 65%, the method is still useful because one can use another enzyme such as an amidase to cleave the benzoylamide enantioselectively to the amino acid. Thus, the overall theoretical yield is revised to a level greater than about 50% as opposed to an ordinary resolution where a yield cannot exceed about 50%. This aspect of the invention is illustrated by the following equation:

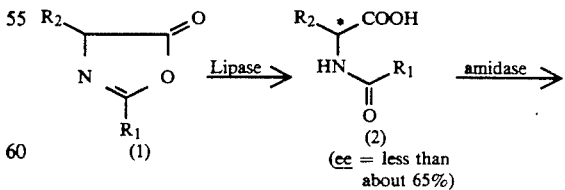

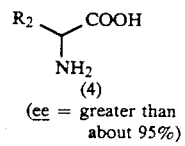

Those skilled in the art Will appreciate that the method of this invention can be practiced with a wide variety, and many different combinations, of conditions, starting oxazolones and enzymes.

The following Examples are presented by way of illustration only and are not in any way to be construed as limiting the scope of the invention defined in the appended claims.

EXAMPLE 1

To a suspension of *Aspergillus niger* lipase (50 mg) (Amano AP 151,000 units/g) in 2 ml of 0.2 M phosphate buffer, pH 7.5, was added 50 mg of 2-phenyl-4-benzyloxazolin-5-one ($R_1$=phenyl; $R_2$=benzyl). The reaction mixture was stirred with a magnetic stirrer for 17 hours at 25 degrees C; and was then acidified with HCl and exhaustively extracted with ethyl acetate three times. The combined organic extract was dried over magnesium sulfate and was then evaporated to dryness in vacuo.

The residue was suspended in a small aliquot of chloroform and chromatographed over a silica gel (Baker's 40 flash chromatography) column (1×10 cm). Elution of the column with a solvent mixture consisting of CHCl$_3$-methanol 98:2 to 95 5) gave 35 mg of D-N-benzoylphenylalanine, $[\alpha]^{25}_D$= +24.0 degrees (c, 2.8, CH$_3$OH).

The optical purity of the product was determined by first converting the product to the corresponding ester (diazomethane). The enantiomeric excess (ee) of the ester was determined by $^1$H NMR spectroscopy in the presence of 4.0 equivalents of Eu(hfc)$_3$. The ee was determined to be greater than 99 percent by observing the ratio of the areas of splitting of the CH$_3$ group.

EXAMPLE 2

The procedure of Example 1 was repeated except that porcine pancreatic lipase (50 mg, Fermlipase PL, Genencor) was used as the enzyme. After 45 hours at 25 degrees C, 45 mg of L-N-benzoylphenylalanine was obtained, $[\alpha]^{25}_D$= −23.8 degrees (c, 4.5, CH$_3$OH). The ee was determined to be about 99 percent.

EXAMPLE 3

The procedure of Example 1 was repeated except that 2-phenyl-4-phenyl-oxazolin-5-one ($R_1$=$R_2$=phenyl) was used as the substrate to obtain D-N-benzoylphenylglycine, $[\alpha]^{25}_D$=77 degrees (c, 2.0, CH$_3$OH). The ee was determined to be about 80 percent.

EXAMPLE 4

The procedure of Example 1 was repeated using 2-phenyl-4-phenyl-oxazolin-5-one ($R_1$=$R_2$=phenyl) as the substrate and porcine pancreatic lipase (Fermlipase PL) as the enzyme to obtain L-N-benzoylphenylglycine, $[\alpha]^{25}_D$= −73 degrees (c, 3.5, CH$_3$OH). The ee was determined to be about 76 percent.

EXAMPLE 5

The procedure of Example 1 was repeated using 2-phenyl-4-indolylmethyl-oxazolin-5-one ($R_2$=indolylmethyl) as the substrate to obtain D-N-benzoyltryptophan, $[\alpha]^{25}_D$=13.1 degrees (c, 3.0, CH$_3$OH) (ee =77 percent).

EXAMPLE 6

The procedure of Example 1 was repeated using 2-phenyl-4-indolylmethyl-oxazolin-5-one as the substrate and porcine pancreatic lipase (Fermlipase PL) as the enzyme to obtain L-N-benzoyltryptophan, $[\alpha]^{25}_D$= −16.6 degrees (c, 2.5, CH$_3$OH) (ee=98 percent).

EXAMPLE 7

The procedure of Example 1 was repeated using 2-phenyl-4-isobutyl-oxazolin-5-one ($R_2$= −CH$_2$CH(CH$_3$)$_2$) as the substrate and porcine pancreatic lipase (Fermlipase PL) as the enzyme to obtain L-N-benzoylleucine, $[\alpha]^{25}_D$= −6.6 degrees (c, 4.2, CH$_3$OH) (ee =87 percent).

EXAMPLE 8

The procedure of Example 1 was repeated using 2-phenyl-4-(p-hydroxyphenyl)-oxazolin-5-one ($R_2$=p-hydroxyphenyl) as the substrate and porcine pancreatic lipase (Fermlipase PL) as the enzyme to obtain L-N-benzoly-p-hydroxy-phenylglycine, $[\alpha]^{25}_D$= −49.3 degrees (c, 4.5, CH$_3$OH) (ee=67 percent).

EXAMPLE 9

The procedure of Example 1 was repeated except 2-phenyl-4-methylmercaptoethyl-oxazolin-5-one ($R_2$= −CH$_2$CH$_2$SCH$_3$) was used as the substrate to obtain D-N-benzoylmethionine, $[\alpha]^{25}_D$=14 degrees (c, 2.1, CH$_3$OH) (ee=83 percent).

EXAMPLE 10

The procedure of Example 1 was repeated using 2-phenyl-4-methylmercaptoethyl-oxazolin-5-one ($R_2$= −CH$_2$CH$_2$SCH$_3$) as the substrate and porcine pancreatic lipase (Fermlipase PL) as the enzyme to obtain L-N-benzoylmethionine, $[\alpha]^{25}_D$= −13.9 degrees (c, 4.8, CH$_3$OH) (ee=80 percent).

EXAMPLE II

The procedure of Example 1 was repeated using 2-phenyl-4-(p-hydroxybenzyl)-oxazolin-5-one ($R_2$=benzyl-p-hydroxy) as the substrate to obtain D-N-benzoyltyrosine, $[\alpha]^{25}_D$=11.2 degrees (c, 3.0, CH$_3$OH) (ee=37 percent).

EXAMPLE 12

The procedure of Example 1 was repeated using 2-phenyl-4-(p-methoxy-benzyl)-oxazolin-5-one ($R_2$=benzyl-p-methoxy) as the substrate and porcine pancreatic lipase (Fermlipase PL) as the enzyme (23 degrees C., 46 hr) to obtain 2(R)-benzoylamino-3-(p-methoxyphenyl)propionic acid, $[\alpha]^{25}_D$= −10.4 degrees (c, 4, CH$_3$OH) (ee=52.4 percent).

EXAMPLE 13

The procedure of Example 1 was repeated using 2-phenyl-4-(p-methoxy-benzyl)-oxazolin-5-one ($R_2$=benzyl-p-methoxy) as the substrate (23 degrees C., 46 hr) to obtain 2(S)-benzoylamino-3-(p-methoxyphenyl)propionic acid, $[\alpha]^{25}_D$= +11.0 degrees (c, 3.6, CH$_3$OH) (ee=56.5 percent).

EXAMPLE 14

The procedure of Example 1 was repeated using 2-phenyl-4-(2-furfuryl)-oxazolin-5-one ($R_2$=2-furfuryl) as the substrate (23 degrees C., 24 hr) to obtain 2(S)-benzoylamino-3-(2-furyl)propionic acid, $[\alpha]^{25}_D$= +17.0 degrees (c, 2.7, CH$_3$OH) (ee=85.3 percent).

EXAMPLE 15

The procedure of Example 1 was repeated using 2-phenyl-4-(2-furfuryl)-oxazolin-5-one ($R_2$=2-furfuryl) as the substrate and porcine pancreatic lipase (Fermlipase PL) as the enzyme (23 degrees C., 24 hr) to obtain 2(R)-benzoyl-amino-3-(2-furyl)propionic acid, $[\alpha]^{25}_D = -12.7$ degrees (c, 3.0, $CH_3OH$) ee=60 percent).

EXAMPLE 16

The procedure of Example 1 was repeated using 2-phenyl-4-(2-naphthyl)-oxazolin-5-one ($R_2$=2-naphthyl) as the substrate (23 degrees C., 144 hr) to obtain 2(S)-benzoylamino-3-(2-naphthyl)propionic acid, $[\alpha]^{25}_D = +1.8$ degrees (c, 4.6, $CH_3OH$).

EXAMPLE 17

The procedure of Example 1 was repeated using 2-(2-naphthyl)-oxazolin-5-one ($R_2$=2-naphthyl) as the substrate and porcine pancreatic lipase (Fermlipase PL) as the enzyme (23 degrees C., 144 hr) to obtain 2(R)-benzoylamino-3-(2-naphthyl)propionic acid, $[\alpha]^{25}_D = -0.61$ degrees (c, 4.0, $CH_3OH$).

EXAMPLE 18

The procedure of Example 1 was repeated using 2-phenyl-4-(1-naphthyl-allyl)-oxazolin-5-one ($R_2$=1-naphthyl) as the substrate and porcine pancreatic lipase (Fermlipase PL as the enzyme (23 degrees C., 21 hr) to obtain 2(R)-benzoyl-amino-3-(1-naphthyl)propionic acid, $[\alpha]^{25}_D = -107.5$ degrees (c, 4.2, $CH_3OH$) (ee=85.3 percent).

EXAMPLE 19

The procedure of Example 1 was repeated using 2-phenyl-4-(isopropyl)-oxazolin-5-one ($R_2=-CH(CH_3)_2$) as the substrate (23 degrees C, 24 hr) to obtain D-N-benzoylvaline, $[\alpha]^{25}_D = +0.72$ degrees (c, 3.2, $CH_3OH$).

EXAMPLE 20

The procedure of Example 1 was repeated using 2-phenyl-4-(p-acetoxy-benzyl)-oxazolin-5-one ($R_2$=p-acetoxy-benzyl) as the substrate (23 degrees C., 24 hr) to obtain 2(S)-benzoylamino-3-(p-methoxyphenyl)propionic acid, $[\alpha]^{25}_D = +18.5$ degrees (c, 2.7, $CH_3OH$).

EXAMPLE 21

The procedure of Example 1 was repeated using 2-phenyl-4-(methyl-benzyl)-oxazolin-5-one ($R_2$=p-methylbenzyl) as the substrate (23 degrees C., 24 hr) to obtain -2(S)-benzoylamino-3-(p-methoxyphenyl)propionic acid, $[\alpha]^{25}_D = +11.9$ degrees (c, 3.3, $CH_3OH$) (ee=56.9 percent).

EXAMPLE 22

The procedure of Example 1 was repeated using 2-phenyl-4-(p-methyl-benzyl)-oxazolin-5-one ($R_2$=p-methylbenzyl) as the substrate and porcine pancreatic lipase (Fermlipase PL) as the enzyme (23 degrees C., 24 hr) to obtain L-N-benzoyl-(p-methylphenyl)alanine, $[\alpha]^{25}_D = -13.1$ degrees (c, 3.9, $CH_3OH$) (ee=60.8 percent).

EXAMPLE 23

The procedure of Example 1 was repeated using 2-phenyl-4-(1,4-benzodioxane-6-methylene)-oxazolin-5-one ($R_2$=1,4-benzodioxane) as the substrate (23 degrees C, 30 hr) to obtain D-N-benzoyl-(1,2)-benzo-(1',4'-dioxane)alan $[\alpha]^{25}_D = 2.4$ degrees (c, 4.5, $CH_3OH$) (ee=20 percent).

EXAMPLE 24

The procedure of Example 1 was repeated using 2-phenyl-4-(4-(1,4-benzodioxane-6-methylene))-oxazolin-5-one ($R_2$=1,4 benzodioxane) as the substrate and porcine pancreatic lipase (Fermlipase PL) as the enzyme (23 degrees C, 30 hr) to obtain 2(R)-benzoylamino-3-(6-(1,4-benzodioxane))propionic acid, $[\alpha]^{25}_D = -9.3$ degrees (c, 4.9, $CH_3OH$) (ee=54.5 percent).

EXAMPLE 25

The procedure of Example 1 was repeated using 2-phenyl-4-(3-furfuryl)-oxazolin-5-one ($R_2$=3-furfuryl) as the substrate (23° C., 46 hr) to obtain 2(S)-benzoylamino-3-(3-furfuryl)propionic acid, $[\alpha]^{25}_D = +3.7$ degrees (c, 3.0, $CH_3OH$) (ee=56.5 percent).

EXAMPLE 26

The procedure of Example 1 was repeated using 2phenyl-4-(3-furfuryl)-oxazolin-5-one ($R_2$=3-furfuryl) as the substrate and porcine pancreatic lipase (Fermlipase PL) as the enzyme (23 degrees C., 24 hr) to obtain 2(R)-benzoylamino-3-(3-furyl)propionic acid, $[\alpha]^{25}_D = -1.8$ degrees (c, 4.0, $CH_3OH$) (ee=43 percent).

EXAMPLE 27

The Example of procedure of Example 1 was repeated using 2-phenyl-4-(2-phenyl-ethyl)-oxazolin-5-one as the substrate (23 degrees C. 48 hr) to obtain 2(S)-benzoylamino-3-phenyl-butyric acid, $[\alpha]^{25}_D = +3.6$ degrees (c, 3.3, $CH_3OH$) (ee=29.8 percent).

EXAMPLE 28

The Example of procedure of Example 1 was repeated using 2-phenyl-4-(2-phenyl-ethyl)-oxazolin-5-one as the substrate and porcine pancreatic lipase (Fermlipase PL) as the enzyme (23 degrees C., 48 hr) to obtain 2(R)-benzoylamino-3-phenyl-butyric acid, $[\alpha]^{25}_D = -5.74$ degrees (c, 3.9, $CH_3OH$) (ee=35.3 percent).

EXAMPLE 29

The procedure of Example 1 was repeated using 2-phenyl-4-(2-phenyl-ethyl)-oxazolin-5-one as the substrate and Pseudomonas sp. (AK) as the enzyme (23 degrees C., 48 hr) to obtain 2(R)-benzoylamino-3-phenyl-butyric acid, $[\alpha]^{25}_D = -5.74$ degrees (c, 3.9, $CH_3OH$) (ee=35.3 percent).

EXAMPLE 30

The procedure of Example 1 was repeated using 2-phenyl-4-(2-phenyl-ethyl)-oxazolin-5-one as the substrate and Pseudomonas sp. (P-30), as the enzyme (23 degrees C., 48 hr) to obtain 2(R)-benzoylamino-3-phenyl-butyric acid, $[\alpha]^{25}_D = -3.8$ degrees (c, 3.1, $CH_3OH$) (ee=30.5 percent).

EXAMPLE 31

The procedure of Example 1 was repeated using 2-phenyl-4-(2-phenyl-ethyl)-oxazolin-5-one as the substrate and *Mucor miehei* as the enzyme (23 degrees C., 48 hr) to obtain 2(R)-benzoylamino-3-phenyl-butyric acid, $[\alpha]^{25}_D = -7.4$ degrees (c, 3.9, CH$_3$OH) ee=39.4 percent).

Additional Examples are presented below in Table I. The same procedure as presented in Example 3 where $R_1=R_2=$phenyl was repeated except that the enzyme was varied. Table I demonstrates the wide application of the present invention using various enzymes. As indicated, the lipases are generally preferred for the production of L-amino acids. The proteases can provide a substantial enantiomeric excess of certain D-amino acids.

tinase G obtained from Amano; Prot(A$_6$) refers to Super PECP II obtained from Amano; AP refers to Amano AP (*Aspergillus niger*) sold by Amano; AY refers to *Candida cylindracea* obtained from Amano; PL (Meito) refers to *Alcaligenes sp.* obtained from Meito Sangyo Ltd., Tokyo, Japan; Lipase (Seik) refers to *Rhizopus delemar* obtained from Seikagaku Kogyo Co.; MY refers to *Candida cylindracea* obtained from Meito Sangyo Ltd., Tokyo, Japan; Yeast refers to Red Star yeast available at retail; N refers to *Rhizopus niveus* obtained from Amano; and APF-12 refers to *Aspergillus niger* obtained from Amano.

TABLE I

| No. | ENZYME | TIME HR. | PRODUCT YIELD mg | $[\alpha]^{25}$D DEGREES | ee (%) | CONF. |
|---|---|---|---|---|---|---|
| 1 | AK | 40 | 28 | −13.1 | 55.3 | L |
| 2 | K10 | 72 | 38 | −4.2 | 17.6 | L |
| 3 | P30 | 24 | 35 | −10.8 | 45.4 | L |
| 4 | PPL | 24 | 34 | −21.6 | 92.2 | L |
| 5 | PL (Ferm) | 42 | 45 | −23.6 | >99 | L |
| 6 | MAP | 16 | 28 | −10.9 | 46.0 | L |
| 7 | Prot(2A) | 16 | 32 | +8.4 | 35.4 | D |
| 8 | AY-50 | 64 | 37 | +13.7 | 57.8 | D |
| 9 | FAP | 64 | 23.5 | −5.2 | 22.1 | L |
| 10 | Prot(A$_1$) | 40 | 38 | +23.9 | >99 | D |
| 11 | Prot(A$_6$) | 40 | 27 | +12.2 | 51.6 | D |
| 12 | AP | 17 | 26 | +24 | >99 | D |
| 13 | AY | 42 | 33 | −13.6 | 56.8 | L |
| 14 | PL (Meito) | 17 | 28 | −10.6 | 43.9 | L |
| 15 | Lipase (Seik) | 42 | 33.5 | −7.1 | 29.5 | L |
| 16 | MY | 72 | 45 | +4.25 | 18 | L |
| 17 | YEAST | 20 | 39 | −2.6 | 10.8 | L |
| 18 | N | 64 | 26 | −2.7 | 11.5 | L |
| 19 | APF-12 | 64 | 43 | +2.4 | 10.1 | D |

In Table I, AK refers to the lipase Pseudomonas sp. and obtained from Amano International Enzyme, Troy, VA; K10 refers to Pseudomonas sp. obtained from Amano; P30 refers to the lipase derived from *Pseudomonas cepacia* and obtained from Amano; PPL refers to Porcine pancreatic lipase obtained from Sigma Chemical Co., St. Louis, MO; PL refers to Fermlipase PL sold by Genencor International Inc., San Francisco, CA; MAP refers to *Mucor miehei* obtained from Amano; Prot(2A) (*Aspergillus oryzae*) refers to Protease 2A obtained from Amano; AY-50 refers to *Candida cylindracea* obtained from Amano; FAP refers to *Rhizopus jananicus* obtained from Amano; Prot(A$_1$) refers to Pec- Table II lists information from some of the foregoing Examples with additional Examples being reported at Nos. 9-13 and 15-16. For the results reported, the procedure of Example 1 was repeated where R$_1$ is a phenyl group and R$_2$ is varied as shown. Table II provides a comparison of various R$_2$ substitutions using one of two enzymes (AP or PL) to demonstrate the broad applicability of the present invention. AP refers the protease Amano AP; and PL refers to the lipase Fermlipase PL. As indicated, the protease provides the D-amino acid and the lipase provides the L-amino acid. The ee percentages are among the highest reported for a catalyzed asymmetric hydrolysis of oxazolones.

TABLE II

| No. | R$_2$ GROUP | ENZYME | TIME HR. | $[\alpha]_D^{25}$ DEGREES | ee (%) | CONF. |
|---|---|---|---|---|---|---|
| 1 | CH$_3$SCH$_2$CH$_2$— | AP | 5 | +14.4 | 83.0 | D |
| 2 | CH$_3$SCH$_2$CH$_2$— | PL | 16 | −13.9 | 80.0 | L |
| 3 | p-HO—Ph—CH$_2$— | AP | 20 | +11.2 | 37.0 | D |
| 4 | Ph—CH$_2$— | AP | 17 | +24.0 | >99 | D |
| 5 | Ph—CH$_2$— | PL | 42 | −23.8 | >99 | L |
| 6 | (indolyl)CH$_2$— | AP | 100 | +13.1 | 77 | D |
| 7 | (indolyl)CH$_2$— | PL | 100 | −16.6 | 98 | L |
| 8 | (CH$_3$)$_2$CHCH$_2$— | PL | 18 | −6.6 | 87 | L |

TABLE II-continued

| No. | R₂ GROUP | ENZYME | TIME HR. | $[\alpha]_D^{25}$ DEGREES | ee (%) | CONF. |
|---|---|---|---|---|---|---|
| 9 | 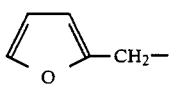 | PL | 20 | −73 | 76 | L |
| 10 | 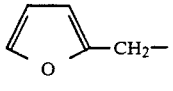 | AP | 20 | +77 | 80 | D |
| 11 | p-HO—PhCH₂— | PL | 20 | −5.7 | 18.9 | L |
| 12 | p-AcO—PhCH₂— | AP | 72 | +11.2 | 37 | D |
| 13 | p-HO—Ph— | AP | 168 | +10.8 | 14.8 | D |
| 14 | p-HO—Ph— | PL | 120 | −49.3 | 67.0 | L |
| 15 | PhCH₂SCH₂— | AP | 90 | +10.1 | 20.0 | D |
| 16 | PhCH₂SCH₂— | PL | 90 | −9.15 | 20 | L |

Table III provides a tabular summary of the reaction conditions and results from Examples 12-18 and 21-29 specified above. The comparison of various R₂ substitutions with two different enzymes (AP and PL) demonstrates the relative effect of the inventive method on each R₂ substitution. For comparative purposes, the last entry shows the comparable results obtained using AK as the enzyme.

TABLE III

| Ex. | R₂ GROUP | ENZYME | TIME HR. | $[\alpha]_D^{25}$ DEGREES | ee (%) | CONF. |
|---|---|---|---|---|---|---|
| 12 | p-CH₃OPhCH₂— | PL | 46 | −10.4 | 52.4 | L |
| 13 | p-CH₃OPhCH₂— | AP | 46 | +11 | 56.5 | D |
| 14 | 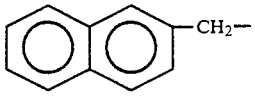 | AP | 24 | +17.0 | 85.3 | D |
| 15 | 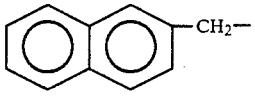 | PL | 24 | −12.7 | 60.0 | L |
| 16 | 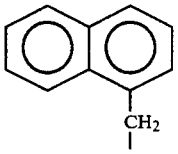 | AP | 144 | +1.8 | — | D |
| 17 | 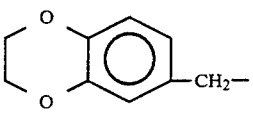 | PL | 144 | −0.61 | — | L |
| 18 | 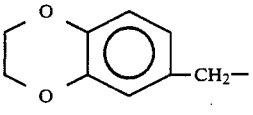 | PL | 21 | −107.5 | 85.3 | L |
| 21 | p-CH₃PhCH₂— | AP | 24 | +11.9 | 56.9 | D |
| 22 | p-CH₃PhCH₂— | PL | 24 | −13.1 | 60.8 | L |
| 23 |  | AP | 30 | +2.4 | 20 | D |
| 24 |  | PL | 30 | −9.3 | 54.5 | L |

TABLE III-continued

| Ex. | R₂ GROUP | ENZYME | TIME HR. | $[\alpha]_D^{25}$ DEGREES | ee (%) | CONF. |
|---|---|---|---|---|---|---|
| 25 | furan-CH₂— | AP | 24 | +3.7 | 56.5 | D |
| 26 | furan-CH₂— | PL | 24 | −1.8 | 43 | L |
| 27 | phenyl-CH₂CH₂— | AP | 48 | −3.6 | 29.8 | D |
| 28 | phenyl-CH₂CH₂— | PL | 48 | −5.0 | 33.3 | L |
| 29 | phenyl-CH₂CH₂— | AK | 48 | −5.7 | 35.3 | L |

It should be understood that various modifications, changes and variations may be made in the details of the present disclosure without departing from the spirit and scope of this invention.

What is claimed is:

1. An enzymatic asymmetric hydrolysis process for preparing an optically-active amino acid in an enantiomeric excess of at least about 65% which comprises subjecting an oxazolone precursor of the amino acid to the presence of a catalytically effective amount of a hydrolytically active lipase in a solvent so as to enantioselectively cleave the oxazolone precursor, and recovering the optically-active amino acid.

2. The process of claim 1 wherein the enzyme is a lipase that is selected from the group consisting of *Aspergillus niger* lipase, porcine pancreatic lipase and *Mucor miehei* lipase.

3. The process of claim 1 wherein the solvent is an aqueous solution having a pH in the range of about 3 to about 10.

4. The process of claim 1 wherein the solvent is an aqueous solution having a pH in the range of about 7 to about 8.

5. The process of claim 1 wherein the concentration of the oxazolone precursor in said solvent is in the range of about 0.1 to about 1 M.

6. The process of claim 1 wherein the method is carried out at a temperature in the range from about 10 to about 40 degrees C.

7. The process of claim 1 wherein the solvent is an organic solvent which does not denature the enzyme.

8. The process of claim 7 wherein the organic solvent is selected from the group consisting of carbon tetrachloride, cyclohexane, carbon disulfide, hexane, polyvinyl alcohol and propylene glycol.

9. The process of claim 1 wherein the oxazolone precursor comprises a 5(4H)-oxazolone having the formula:

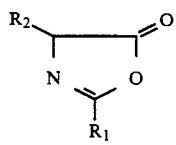

where

R₁ is selected from the group consisting of hydrogen atom; a phenyl group; an alkyl or alkenyl radical of less than ten carbon atoms; an araliphatic radical having a phenyl group and an alkyl group of less than three carbon atoms; an alkyl or alkenyl radical of less than ten carbon atoms substituted with one or two carboxylic acid groups; an araliphatic radical having a phenyl group and an alkyl group of less than three carbon atoms substituted by one or two carboxylic acid groups; an alkyl or alkenyl radical of less than ten carbon atoms substituted by one or two ester groups; an araliphatic radical having a phenyl group and an alkyl group of less than three carbon atoms substituted by one or two ester groups; an alkyl or alkenyl radical of less than ten carbon atoms substituted with one or more carboxylic acid esters; and an araliphatic radical having a phenyl group and an alkyl group of less than three carbon atoms substituted with one or more carboxylic acid esters; and R₂ is selected from the group consisting of a phenyl group; an alkyl or alkenyl radical of less than ten carbon atoms; and araliphatic radical having a phenyl group and an alkyl group of less than six carbon atoms; and a heterocyclic radical derived from a heterocyclic compound that is selected from the group consisting of indole, pyrrole, isoindole, indolizine, furan, benzofuran, pyridazine, triazole, thiazole, oxazole, pyrazole, isoxazole, isothiazole, thiophene, pyridine and indoline.

10. The process of claim 9 wherein $R_1$ is an alkyl or alkenyl radical which includes less than ten carbon atoms and a halogen.

11. The process of claim 10 wherein the halogen is fluorine or chlorine.

12. The process of claim 9 wherein $R_1$ is a phenyl group.

13. The process of claim 9 wherein $R_2$ is either (a) an alkyl or alkenyl radical which includes less than ten carbon atoms, or (b) a member of the group consisting of sulfur, a nitrogen group, oxygen and a halogen.

14. The process of claim 12 wherein $R_2$ is either (a) an alkyl or alkenyl radical which includes less than ten carbon atoms or (b) fluorine or chlorine.

15. The process of claim 9 wherein $R_2$ is an araliphatic radical having a phenyl group and an alkyl group of less than six carbon atoms further comprising substitution of the phenyl group by a member of the group consisting of a halogen, a nitrogen group, sulfur, a methoxy group, a hydroxy group and oxygen.

16. The process of claim 9 wherein $R_2$ is a phenyl group or a benzyl group.

17. The process of claim 9 wherein $R_2$ is a heterocyclic radical which includes a member of the group consisting of an alkyl radical of less than five carbon atoms, an alkenyl radical of less than five carbon atoms and a halogen.

18. The process of claim 9 wherein $R_2$ is a heterocyclic radical which includes fluorine or chlorine.

19. The process of claim 9 wherein $R_1$ is a phenyl group and $R_2$ is a member selected from the group consisting of phenyl, benzyl, indolyl, methoxyphenyl, a thioalkyl, methoxyindolyl, alkyl and branched allyl.

20. An optically-active amino acid made in accordance with the process of claim 1.

21. An enzymatic asymmetric hydrolysis process for preparing an optically-active amino acid which comprises subjecting a 5(4H)-oxazolone to the hydrolytic enzymatic action of a lipase present in a catalytically effective amount in a solvent and recovering the desired optically-active amino acid, wherein the [5(H)-oxazolone] 5(4H)-oxazolone has the formula:

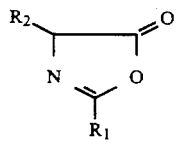

where
$R_1$ is selected from the group consisting of a hydrogen atom; a phenyl group; an alkyl or alkenyl radical of less than ten carbon atoms; an araliphatic radical having a phenyl group and an alkyl group of less than three carbon atoms; an alkyl or alkenyl radical of less than ten carbon atoms substituted with one or two carboxylic acid groups; an araliphatic radical having a phenyl group and an alkyl group of less than three carbon atoms substituted by one or two carboxylic acid groups; an alkyl or alkenyl radical of less than ten carbon atoms substituted by one or two ester groups; an araliphatic radical having a phenyl group and an alkyl group of less than three carbon atoms substituted by one or two esters; an alkyl or alkenyl radical of less than ten carbon atoms substituted with one or more carboxylic acid esters; and an araliphatic radical having a phenyl group and an alkyl group of less than three carbon atoms substituted with one or two carboxylic acid esters; and $R_2$ is selected from the group consisting of a phenyl group; an alkyl or alkenyl radical of less than ten carbon atoms; an araliphatic radical having a phenyl group and an alkyl group of less than six carbon atoms; and a heterocyclic radical derived from a heterocyclic compound that is selected from the group consisting of indole, pyrrole, isoindole, indolizine, furan, benzofuran, pyridazine, triazine, thiazole, oxazole, pyrazole, isoxazole, isothiazole, thiophene, pyridine and indoline.

22. The process of claim 21 wherein $R_1$ is an alkyl or alkenyl radical which includes less than ten carbon atoms and a halogen.

23. The process of claim 22 wherein the halogen is fluorine or chlorine.

24. The process of claim 21 wherein $R_1$ is a phenyl group.

25. The process of claim 21 wherein $R_2$ is either (a) an alkyl or alkenyl radical which includes less than ten carbon atoms or (b) a member of the group consisting of sulfur, a nitrogen group, oxygen and a halogen.

26. The process of claim 21 wherein $R_2$ is an alkyl or alkenyl radical which includes less than ten carbon atoms and fluorine or chlorine.

27. The process of claim 21 wherein $R_2$ is an araliphatic radical having a phenyl group and an alkyl group of less than six carbon atoms further comprising substitution of the phenyl group by a member of the group consisting of a halogen, a nitrogen group, sulfur, a methoxy group, a hydroxy group and oxygen.

28. The process of claim 21 wherein $R_2$ is a phenyl group or a benzyl group.

29. The process of claim 21 wherein $R_2$ is a heterocyclic radical which includes a member of the group consisting of an alkyl radical of less than five carbon atoms, an alkenyl radical of less than five carbon atoms and a halogen.

30. The process of claim 29 wherein $R_2$ is a heterocyclic radical which includes fluorine or chlorine.

31. The process of claim 21 wherein $R_1$ is a phenyl group and $R_2$ is a member selected from the group consisting of phenyl, benzyl, an indolyl, a methoxyphenyl, a thioalkyl, a methoxyindolyl, an-alkyl and a branched allyl.

32. The process of claim 21 wherein the lipase is selected from the group consisting of *Aspergillus niger* lipase, porcine pancreatic lipase and *Mucor miehei* lipase.

33. The process of claim 21 wherein the optically-active amino acid is prepared in an enantiomeric excess of at least 65 percent.

34. The process of claim 21 wherein the optically-active amino acid is prepared in an enantiomeric excess of at least 90 percent.

35. The process of claim 21 wherein the concentration of the oxazolone is in the range of 0.1 to about 1 M.

36. The process of claim 21 wherein the 5(4H)-oxazolone is a racemic mixture and the subjecting step includes stirring and is continued until hydrolysis of the 5(4H)-oxazolone is substantially complete.

37. An optically-active amino acid made in accordance with the process of claim 21.

* * * * *